United States Patent [19]

Bradford

[11] Plant 5,085

[45] Aug. 16, 1983

[54] ALMOND TREE ("WES-MAR")

[76] Inventor: Wesley Bradford, P.O. Box 941, Alamogordo, N. Mex. 88310

[21] Appl. No.: 366,992

[22] Filed: Apr. 9, 1982

[51] Int. Cl.[3] ..... A01H 5/03
[52] U.S. Cl. ..... Plt./30
[58] Field of Search ..... Plt./30

*Primary Examiner*—Robert E. Bagwill

*Attorney, Agent, or Firm*—Roger B. Webster

[57] ABSTRACT

An almond tree which is medium size, vigorous, sturdy, spreading, and dense; abundantly foliated with large, lanceolate, acutely pointed leaves having a finely serrate margin, and small, green, globose glands; blooms heavily with white flowers; and, with medium productivity, is a regular bearer of small, well-sealed nuts having a small, plump, sweet kernel.

1 Drawing Figure

BACKGROUND OF THE VARIETY

1. Field of the Invention

In the course of the maintenance of an almond orchard on my ranch located near Atwater, Merced County, Calif., I frequent such orchard for the purpose of inspection, cultivation, and irrigation, and—against the background of such activities—the present variety of almond tree was discovered.

2. Classification of the Variety

The present new and distinct variety of almond tree is embraced by Class 30, Plants, of the United States Patent Office Manual of Classification.

PRIOR VARIETIES

Among the existent varieties of almond trees which are known to me, and mentioned herein, are Nonpareil (unpatented) and Carmel (U.S. Plant Pat. No. 2,641).

ORIGIN OF THE VARIETY

The present variety of almond tree was discovered by me—during my activities in the maintenance of my aforesaid almond orchard—and which is interplanted with Nonpareil and Carmel varieties—as a chance seedling growing on an adjacent ditch bank. Because of its apparent vigorous growth, I permitted such chance seedling to grow, and subsequently its bloom attracted my attention particularly in that the bloom was heavy and of substantially identical bloom-time with the adjacent Carmel trees. Further, in maturity, such chance seedling bore nuts quite distinctive from those of the Carmel. Thus, with the possibility that such chance seedling would cross-pollinate with the Carmel (which later proved correct), and as the nuts from such chance seedling had commercial potential, I determined to asexually reproduce such chance seedling.

ASEXUAL REPRODUCTION OF THE VARIETY

Such chance seedling (i.e., the present variety of almond tree) was—by budding—asexually reproduced on my behalf by a commercial nursery, and such reproductions, in maturity, ran true in all respects to such chance seedling.

SUMMARY OF THE VARIETY

The present variety of almond tree is characteristically of medium size, vigorous, sturdy, spreading, and dense; abundantly foliated with large, lanceolate, acutely pointed leaves having a finely serrate margin, and small, green, globose glands; blooms heavily with white flowers; and, with medium productivity, is a regular bearer of small, well-sealed nuts having a small, plump, sweet kernel.

The present variety of almond tree is further and more particularly characterized by a substantially identical bloom-time with the Carmel and which assures against some crop diminution when cross-pollenizing varieties have lapped but somewhat staggered bloom-times which results, for example, in the earliest blooms of one of the cross-pollenizers not being properly pollenized. This disadvantage is substantially wholly eliminated by the employment of the present variety as a cross-pollenizer with the Carmel. Also, the present variety serves as well as the Carmel as a cross-pollenizer for the Nonpareil.

The present variety of almond tree is still further characterized, in comparison to the Carmel, by nuts which have more uniform spacing throughout the tree and in distinction to the Carmel which has heavy clusters with the nuts commonly in contact with each other; by nuts which are much shorter and more round than the slender, tapered nuts of the Carmel; by nuts having more pits in the cork; by nuts whose kernels are short and plump whereas the kernels of the Carmel are quite elongated; and by nuts having a pellicle which is darker brown than that of the Carmel.

BRIEF DESCRIPTION OF THE DRAWING

The drawing is an illustration, by photographic reproduction in color, of a twig with leaves and nuts in hull; a twig with leaves; nuts out of hull; and kernels out of shell.

DESCRIPTION OF THE VARIETY

The botanical details of this new and distinct variety of almond tree—with color definitions (except those in common color terms) referenced to Maerz and Paul Dictionary of Color (First Edition)—are as follows:

Tree:
- *Density.*—Dense.
- *Size.*—Medium.
- *Vigor.*—Vigorous.
- *Growth.*—Sturdy.

Trunk:
- *Form.*—Stocky.
- *Texture.*—Medium.

Branches:
*Form.*—Stocky.
*Texture.*—Smooth.
*Lenticels.*—Medium — Small.
*Branching habit.*—Spreading.
*Color.*—New wood: Brown. Mature wood: Dull brown.

Foliage:
*Quantity.*—Abundant.

Leaves:
*Size (mature).*—Large. Average length — 4.31". Average width — 1.02".
*Shape.*—Lanceolate. Acutely pointed.
*Thickness.*—Thin.
*Texture.*—Smooth.
*Margin.*—Finely serrate.
*Petiole.*—Medium length. Slender.
*Glands.*—Average number — 1. Small. Globose. Green. Positioned on petiole near blade.
*Stipules.*—None.
*Color.*—Top Side — Medium green (22-K-7). Under Side — Lighter green (22-H-7).

Bloom:
*Amount of bloom.*—Heavy.
*Color.*—White.
*Blooming period.*—Medium. Substantially identical bloom-time with Carmel.

Crop:
*Bearing.*—Regular bearer.
*Productivity.*—Medium.
*Distribution of nuts on tree.*—Well distributed.
*Harvest period.*—Sept. 3, 1981. Medium, as compared to Nonpareil.
*Tenacity.*—Hangs well on tree. Easy to harvest. Easy to hull.

Hull:
*Outer surface.*—Smooth.
*Form.*—Regular.
*Thickness.*—Thin.
*Flesh.*—Tough.
*Suture.*—Flat.
*Color.*—Light yellow green (21-J-5) with silvery sheen.
*Dehiscence.*—Opens freely.
*Splitting.*—Along suture. Freely at base.

Nut:

*Size.*—Small. Average length — 28.95 mm. Average width — 19.55 mm. Average thickness — 15.7 mm. Average weight — 11.6 per ounce.
*Form.*—Length/Width.— Ovate. Width/Thickness — Plump.
*Shell.*—Soft. Thick. Smooth. Outer shell — Crumbling. Inner shell — Soft. Well sealed.
*Color.*—Medium light brown (13-J-7).
*Pits.*—Small. Numerous. Shallow. Round.
*Base.*—Ventrally oblique.
*Stem scar.*—Small. Acute.
*Apex.*—Acute. Sharp. Shouldered.
*Wing.*—Narrow. Thin. Tapered toward base.
*Inner surface.*—Medium colored.
*Ventral streak.*—Light. Narrow. Long. Point acute.
*Percentage of kernel to nut.*—50.8%.

Kernel:
*Size.*—Small. Average length — 20.8 mm. Average width — 13.85 mm. Average thickness — 9.6 mm. Average weight — 33 per ounce.
*Form.*—Length/Width — Ovate. Width/Thickness — Plump.
*Base.*—Ventrally oblique.
*Stem scar.*—Small.
*Apex.*—Acute. Sharp. Shouldered.
*Texture.*—Wrinkled.
*Pellicle.*—Thin.
*Pubescence.*—Smooth. Veined.
*Color.*—Medium brown (13-L-9).
*Number of doubles.*—Medium.
*Defective kernels (gummy and blanks).*—Few.
*Flavor.*—Sweet.
*Quality.*—Good.

Resistance to insects and diseases: No more susceptible than any usual commercial variety, particularly the Nonpareil.

The almond tree and its nuts herein described may vary in slight detail due to climatic and soil conditions under which the variety may be grown; the present description being of the variety as grown in the Central Valley of California.

I claim:

1. A new and distinct variety of almond tree, substantially as illustrated and described, particularly characterized by substantially identical bloom-time and cross-pollenizing with the Carmel; and by regular bearing of small, well-sealed nuts having a small, plump, sweet kernel.

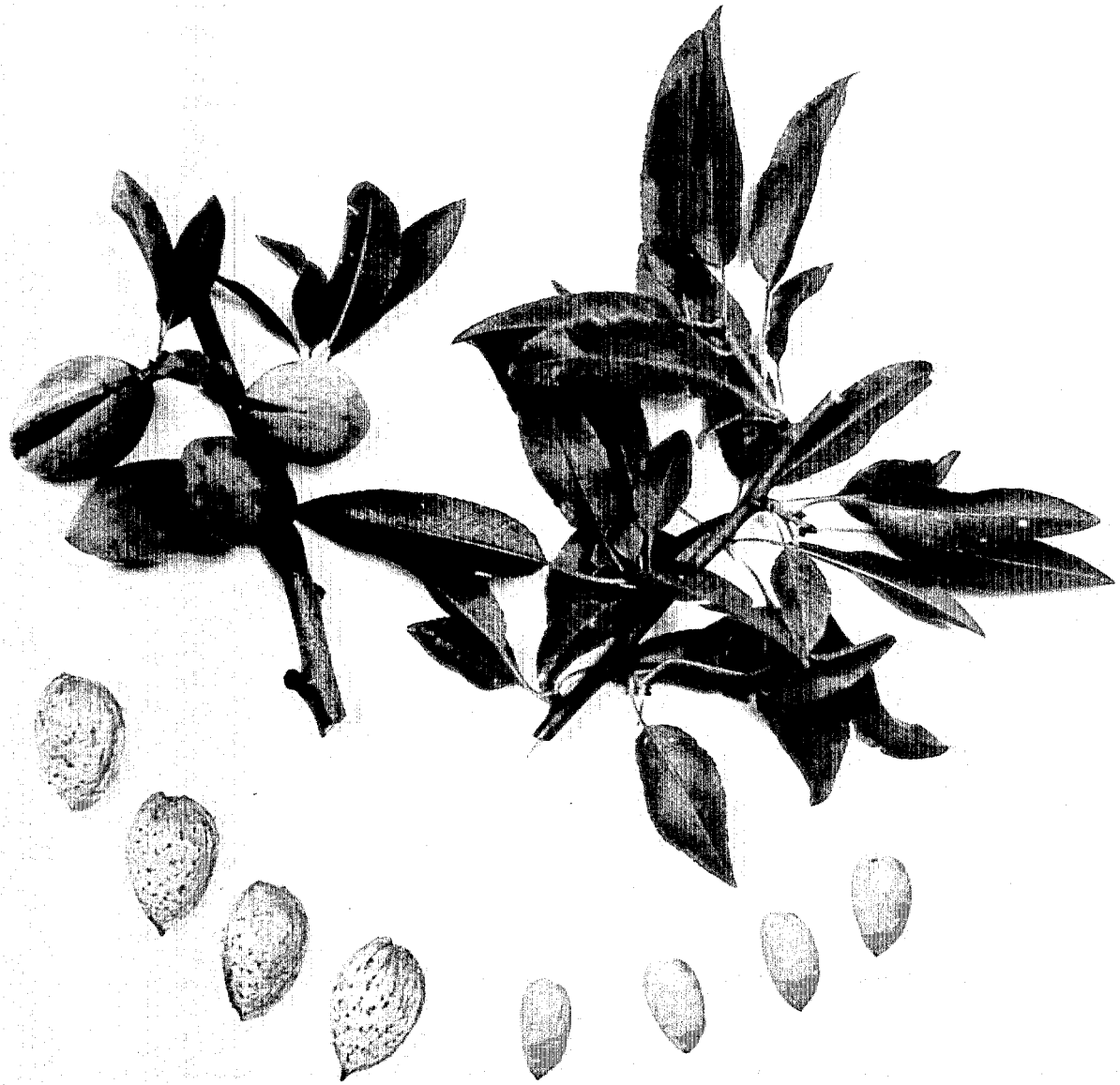

* * * * *